(12) United States Patent
Rolsted et al.

(10) Patent No.: US 10,807,287 B2
(45) Date of Patent: Oct. 20, 2020

(54) METHOD FOR MANUFACTURING OF URINARY CATHETERS

(71) Applicants: COLOPLAST A/S, Humlebaek (DK); ROLSTED MOULD SYSTEM ApS, Farum (DK); Erik Rolsted, Farum (DK); Jakob Øelund, Allerød (DK); Lars Olav Schertiger, Fredensborg (DK); Preben Luther, Birkerød (DK); Kim Bager, Lyngby (DK)

(72) Inventors: Erik Rolsted, Farum (DK); Jakob Øelund, Allerød (DK); Lars Olav Schertiger, Fredensborg (DK); Preben Luther, Birkerød (DK); Kim Bager, Lyngby (DK)

(73) Assignee: COLOPLAST A/S, Humlebaek (DK)

( * ) Notice: Subject to any disclaimer, the term of this patent is extended or adjusted under 35 U.S.C. 154(b) by 841 days.

(21) Appl. No.: 14/381,110

(22) PCT Filed: Feb. 25, 2013

(86) PCT No.: PCT/EP2013/053676
§ 371 (c)(1),
(2) Date: Aug. 26, 2014

(87) PCT Pub. No.: WO2013/127725
PCT Pub. Date: Sep. 6, 2013

(65) Prior Publication Data
US 2015/0051587 A1 Feb. 19, 2015

(30) Foreign Application Priority Data

Feb. 27, 2012 (DK) .................................. 2012 00156
Jan. 31, 2013 (DK) .................................. 2013 00061

(51) Int. Cl.
*B29C 45/26* (2006.01)
*A61M 25/00* (2006.01)
(Continued)

(52) U.S. Cl.
CPC ....... *B29C 45/261* (2013.01); *A61M 25/0009* (2013.01); *A61M 25/0017* (2013.01);
(Continued)

(58) Field of Classification Search
CPC ........... A61M 25/0009; B29C 45/0046; B29C 45/1703; B29C 45/2703; B29C 45/04;
(Continued)

(56) References Cited

U.S. PATENT DOCUMENTS 2,443,053 A * 6/1948 Parmelee .............. B29C 45/261
264/150
3,901,965 A * 8/1975 Honeyman, III . A61M 25/1027
264/275
(Continued)

FOREIGN PATENT DOCUMENTS

CN 1730120 A 2/2006
CN 201 132 011 10/2008
(Continued)

OTHER PUBLICATIONS

International Search Report for International Application No. PCT/EP2013/053676 dated Jun. 28, 2013 (2 pages).
(Continued)

*Primary Examiner* — Matthew J Daniels
*Assistant Examiner* — Andrew D Graham
(74) *Attorney, Agent, or Firm* — Merchant & Gould P.C.

(57) ABSTRACT

A method for manufacturing an elongated element (200) is provided. The method comprises arranging a molding cavity (101), defined by a mold (103) and a mold insert (104), said mold insert (104) comprising a mold core (105) and a
(Continued)

displaceable mold cavity wall (106), said displaceable mold cavity wall (106) being arranged between the mold (103) and the mold core (105), such that the molding cavity has a start volume in a start position of the displaceable mold cavity wall (106). Then a liquid material is injected into a proximal end (102) of the molding cavity (101), where after the displaceable mold cavity wall (106) is displaced in relation to and along with the mold (103) and the mold core (105), distally during said injection, to increase the molding cavity volume from the start volume into an end volume at an end position of the displaceable mold cavity wall (106), wherein the molding cavity (101) in said end position of the displaceable mold cavity wall (106) corresponds to the elongated element (200). The liquid material is solidified, such that the elongated element (200) is formed, and the elongated element (200) and mold insert (104) is removed from said mold (103), where after the elongated element (200) is removed from said mold insert (104). An elongated element and a mold assembly for the manufacture thereof are also provided.

15 Claims, 7 Drawing Sheets

(51) Int. Cl.
| | |
|---|---|
| *B29C 45/43* | (2006.01) |
| *B29C 45/56* | (2006.01) |
| *A61M 39/10* | (2006.01) |
| *B29C 45/00* | (2006.01) |
| *B29C 45/80* | (2006.01) |
| *B29L 31/00* | (2006.01) |
| *B29L 23/00* | (2006.01) |

(52) U.S. Cl.
CPC ......... *A61M 39/10* (2013.01); *B29C 45/0046* (2013.01); *B29C 45/2628* (2013.01); *B29C 45/43* (2013.01); *B29C 45/56* (2013.01); *B29C 45/80* (2013.01); *A61M 2202/0496* (2013.01); *A61M 2207/10* (2013.01); *B29C 2045/5695* (2013.01); *B29L 2023/001* (2013.01); *B29L 2031/7542* (2013.01)

(58) Field of Classification Search
CPC ............ B29C 45/332; B29C 45/14262; B29C 2045/14139; B29C 2045/1719; B29C 33/123; B29C 33/14; B29C 45/261; B29C 45/56; B29C 45/572; B29C 45/80; B29C 2045/0049; B29C 2045/366; B29C 2045/563
See application file for complete search history.

(56) References Cited

U.S. PATENT DOCUMENTS

| | | | | |
|---|---|---|---|---|
| 4,246,225 A * | 1/1981 | Ninneman | .............. | B29C 35/16 264/336 |
| 4,332,545 A * | 6/1982 | Cargile | .................. | B29C 45/36 249/148 |
| 4,516,969 A * | 5/1985 | Kintner | .................. | A61M 3/00 604/187 |
| 4,743,420 A * | 5/1988 | Dutt | .................... | B29C 45/0046 264/102 |
| 4,956,143 A * | 9/1990 | McFarlane | ........ | B29C 45/14598 264/334 |
| 5,240,397 A * | 8/1993 | Fay | ........................ | B29C 45/261 264/328.11 |
| 6,203,528 B1 * | 3/2001 | Deckert | ................ | A61M 39/08 604/131 |
| 6,887,417 B1 * | 5/2005 | Gawreluk | ......... | A61M 25/0009 264/328.1 |
| 6,974,557 B1 * | 12/2005 | Webler | ................. | A61B 5/0084 264/261 |
| 2002/0108614 A1 * | 8/2002 | Schultz | ............... | A61M 1/0047 128/207.14 |
| 2005/0033237 A1 * | 2/2005 | Fentress | ............ | A61M 25/0009 604/165.03 |
| 2005/0253301 A1 * | 11/2005 | Kraenzle | ............... | B29C 45/261 264/328.1 |
| 2007/0224309 A1 * | 9/2007 | Mejlhede | .......... | A61M 25/0009 425/577 |
| 2008/0251963 A1 * | 10/2008 | Steiner | .................... | B29C 45/56 264/151 |
| 2008/0271870 A1 * | 11/2008 | Yotsutsuji | ............. | B29C 45/261 164/132 |
| 2009/0022845 A1 * | 1/2009 | Mai | ..................... | B29C 45/2602 425/595 |
| 2009/0264866 A1 * | 10/2009 | Powell | .............. | A61M 25/0097 604/533 |
| 2010/0092706 A1 * | 4/2010 | Clarke | .................. | B29C 45/561 428/35.7 |
| 2010/0327492 A1 * | 12/2010 | Sansoucy | .......... | A61M 25/0009 264/328.7 |
| 2011/0079138 A1 * | 4/2011 | Storrie | ................... | G01D 5/145 91/1 |
| 2011/0224649 A1 * | 9/2011 | Duane | ............... | A61M 25/0009 604/523 |
| 2011/0254202 A1 * | 10/2011 | Aeschlimann | ........ | A61M 5/158 264/328.1 |
| 2012/0008183 A1 * | 1/2012 | Hara | .................... | B29C 45/1704 359/205.1 |

FOREIGN PATENT DOCUMENTS

| | | | |
|---|---|---|---|
| CN | 201346250 Y | 11/2009 | |
| GB | 2 230 702 | 10/1990 | |
| WO | WO-2010071939 A1 * | 7/2010 | ............ A61M 5/158 |
| WO | WO 2010/149175 | 12/2010 | |
| WO | WO 2010149175 A1 * | 12/2010 | ........ A61M 25/0015 |

OTHER PUBLICATIONS

Chinese Search Report for CN Application No. 2017107745061 dated Dec. 4, 2019 (2 pages).
Chinese Office Action for CN Application No. 2017107745061 dated Dec. 4, 2019 (7 pages).

* cited by examiner

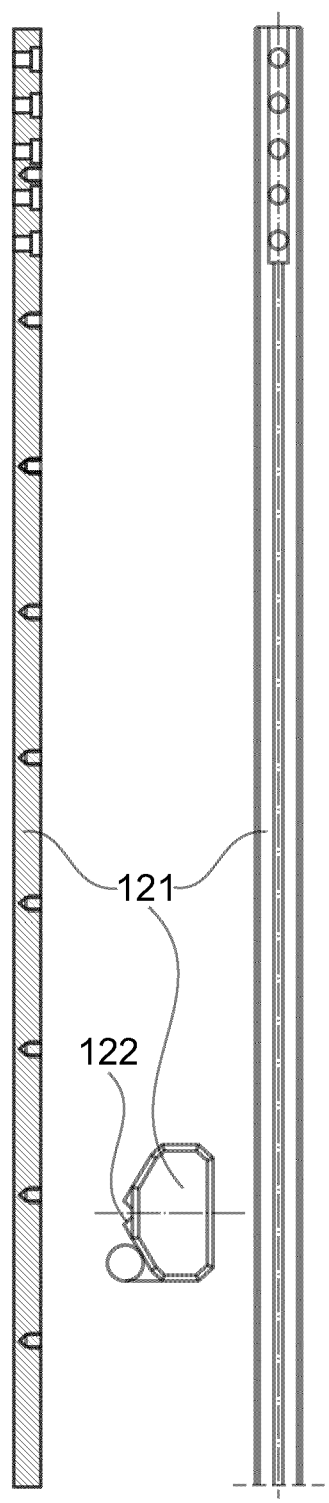
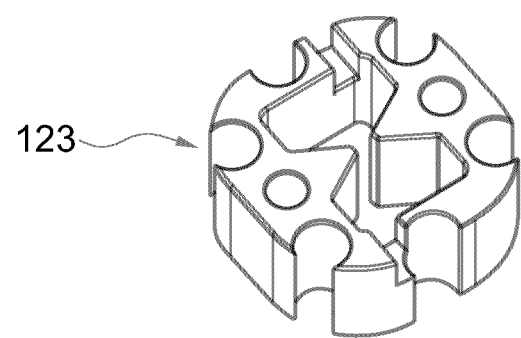
Fig. 6
Fig. 7

METHOD FOR MANUFACTURING OF URINARY CATHETERS

This application is a National Stage Application of PCT/EP2013/053676, filed 25 Feb. 2013, which claims benefit of Serial No. PA2012 00156, filed 27 Feb. 2012 in Denmark and Serial No. PA2013 000061, filed 31 Jan. 2013 in Denmark and which applications are incorporated herein by reference. To the extent appropriate, a claim of priority is made to each of the above disclosed applications.

FIELD OF THE INVENTION

This invention pertains in general to the field of injection molding of thin-walled, elongated, elements, with a tubular body and an optionally substantially closed end. More particularly the invention relates to a catheter, such as a urinary catheter, with an elongated tubular portion and a tip portion. Furthermore, the present invention pertains to a method of manufacturing such elements and catheters, and an assembly for forming a molding cavity.

BACKGROUND OF THE INVENTION

Urinary catheters are widely used by persons who have problems with respect to unintentional/intentional emptying of the urinary bladder. A wide variety of different types of urinary catheters is available to individuals or medical professionals, which are specifically designed for a specific use, such as intermittent catheters or permanent/long term catheters, such as Foley catheters.

Intermittent catheters are for example used by individuals who are paralyzed, where the urinary bladder is emptied in regular intervals. These individuals are often capable of inserting the intermittent catheter without assistance. The use of permanent or long-term catheters is usually linked to an individual's hospital stay or at least where the individual is under regular observation of medical professionals, as permanent catheters are not well adapted for self catheterization since they are usually very flexible and have a larger diameter than intermittent catheters. This calls for insertion by medical professionals under relatively clean or even sterile conditions.

Urinary catheters are generally known to comprise a tubular portion for providing a fluid pathway from the urinary bladder to the outside of the body, a tip portion—often rounded—for facilitated insertion of the catheter into the urethra, and drainage openings for facilitating the entering of urine into the tubular portion. At the other end of the tubular portion in relation to the tip portion, a connecting portion may be provided for connection to a urinary bag or other urine discarding means.

The most common method of producing urinary catheters, especially intermittent catheters, is to extrude a tubular portion in a plastic material, and in separate stages providing the tubular portion with the tip portion and drainage openings, and optionally also a connecting portion, such as a portion with somewhat larger diameter, for example a conical portion, at the other end of the tubular portion in relation to the tip portion and drainage openings. Catheters that are manufactured using the extrusion process have a uniform and constant diameter on both the external and the internal surface from end to end, and therefore have a constant thickness of material throughout the entire length of the catheter tube.

Lately, urinary catheters have been injection molded for the omission of unnecessary manufacturing steps. Injection molding of urinary catheters is however accompanied with several obstacles. Due to the delicate dimensions of a urinary catheter, such as small tube diameter and wall thickness while being relatively long, also the mold insert/core, forming the lumen of the tubular portion, needs to be thin and long. When the molten plastic material enters the molding cavity, often under high pressure, the plastic material will whirl in the cavity. Due to the whirling the insert/core will vibrate during the molding process, whereby the diameter of the lumen and the wall not will be unitary along the length of the urinary catheter. This renders the separation of the molded catheter and the insert/core almost impossible, naturally resulting in useless manufacturing in an industrial scale.

GB 2230702 discloses a method for the production of an intermittent urethral catheter, said method comprising injection molding, wherein pins, forming the drainage openings, also stabilize the insert/core in the injection molding cavity.

However, even though the insert/core is somewhat stabilized, still the insert/core along its length from the drainage openings to the end of molding cavity, which normally constitutes approximately 90% of its length, may vibrate. Additionally, even though the stabilization of the insert/core helps the formation of a tubular wall with unitary dimensions, it may be very difficult to separate the insert/core from the molded catheter, due to the large contact surface between the insert/core and the plastic material. This problem is specifically significant when the injected material is a plastic material with high adherence properties, which is often the case with plastic materials with well-suited flexibility properties for the intended purpose. Such materials may for example be polyurethanes.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a method for manufacturing an elongated element, comprising the steps of arranging a molding cavity, defined by a mold a mold insert, said mold insert comprising a mold core and a displaceable mold cavity wall, said displaceable mold cavity wall being arranged between the mold and the mold core, such that the molding cavity has a start volume in a start position of the displaceable mold cavity wall; injecting a liquid material into a proximal end of the molding cavity; displacing the displaceable mold cavity wall, in relation to and along with the mold and the mold core, distally during said injection, to increase the molding cavity volume from the start volume into an end volume at an end position of the displaceable mold cavity wall, wherein the molding cavity in said end position of said displaceable mold cavity wall corresponds to the elongated element; solidifying said liquid material, such that the elongated element is formed; removing said elongated element and mold insert from said mold; and removing said elongated element from said mold insert.

An elongated element manufactured with this method and a mold assembly for realizing such method is also provided.

Further advantageous embodiments of the present invention are embodied in the appended patent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which

FIG. 6 is a side view, a longitudinal cross sectional as well as a top/bottom view of a longitudinal support elements of a core guide support, according to one embodiment of the present invention;

FIG. 7 is a perspective view of a shaft stay according to one embodiment of the present invention.

DESCRIPTION OF EMBODIMENTS

The following description focuses on an embodiment of the present invention applicable to an elongated element, and in particular to a urinary catheter, and more specifically an intermittent urinary catheter. However, it will be appreciated that the invention is not limited to this application but may be applied to many other elongated elements, such as Foley catheters or test tubes, etc.

In specific alternative embodiments, the elongated element according to the present invention may for examples be tubes with snap or friction couplings at both ends, balloon catheters, containers, syringes, pipettes, or test tubes. With regard to tubes with snap or friction couplings at both ends, these may be realized with a male coupling at one end and a female coupling in the other end, such that a multitude of such tubes may be interconnected in series, while maintaining a through channel through the interconnected series of tubes. In this way a series of tubes can be assembled to define longer tubes. The snap coupling could in an embodiment be of the bayonet-type coupling. The tubes can be used for plumbing, for petrol for a filling a tank on a boat, and for toys. With regard to balloon catheters, these balloon catheters may be used for anal or stomal irrigation. Such a balloon catheter includes two channels, one for liquid and one for inflation of the balloon—typically with air. The liquid channel terminates in two eyelets and the air channel terminates in one inflation hole situated under the balloon. In the end opposite the tip, the air channel and liquid channel terminates in a connector. The balloon may be welded or glued onto the catheter following the injection molding process. With regard to containers, the present invention may also be used to mold a container, such as for example for a catheter, in form of a tubular container having a slightly conical shape (like Coloplast Compact Male container). With regard to syringes, pipettes, test tubes, these products may also be manufactured with a mold assembly according to the embodiments disclosed herein, with minor product specific adaptations, which are readily known to the skilled artisan. In the context herein the terms "proximal" and "distal", and analogues thereof, are used in relation to the body on which the end product is to be used, while the terms "lateral" and "central" are used in relation to the longitudinal as well as the proximodistal extension of the end product. This means that also with respect of molds and mold assemblies these terms are used in relation to the end product characteristics.

Figure 1:
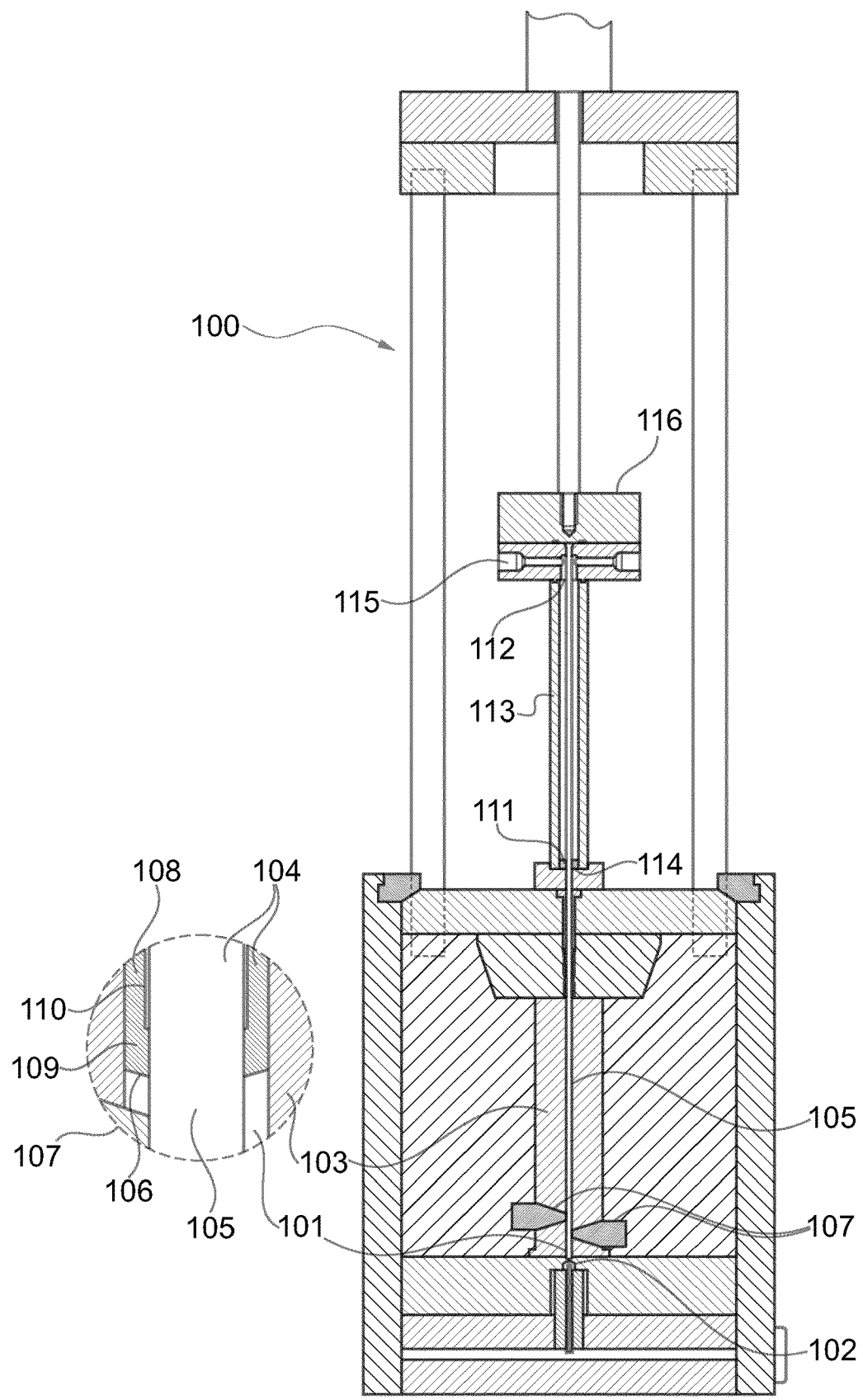
FIG. 1 is across-sectional view of a mold assembly according to one embodiment of the present invention.

In FIG. 1 a mold assembly 100 for the manufacturing of a urinary catheter, according to an embodiment is disclosed. FIG. 1 illustrates a start position for the manufacturing of a urinary catheter. A material hopper (not shown) is connected in fluid communication with an injection ram or screw-type plunger (not shown), and a heating unit (not shown), in a known manner with respect of injection molding. The injection ram or screw plunger is in turn in fluid communication with a mold cavity 101 via an injection sprout 102. In this way, a material intended to constitute the urinary catheter may be placed in the material hopper, and then being processed to be injected in a fluid form into the mold cavity 101 via the injection sprout 102. A material being well-functioning for urinary catheters and to possible to use during manufacturing of a urinary catheter according to the methods according to the present invention is polyurethane, despite the stickiness of polyurethanes with regard to metal parts, such as metal mold parts. It is within the ambit of the present invention to inject more than one material and/or different colors of the injected material(s). In this way, different parts of the catheter may be provided with varying flexibility and rigidity, stickiness, depending on the different materials, and the catheter may be provided with color extension indications, such that the user more easily can identify the correct/optimal position of the catheter, without pushing and pulling the catheter back and forth while observing the flow of urine through the catheter, which is a common procedure. In one specific embodiment a first polymeric material is injected, said first polymeric material being intended to form the distal connecting portion of the catheter, where after a second polymeric material is injected, said second polymeric material being intended to form the elongated tubular body of the catheter, wherein said first polymeric material is a more rigid polymeric material than said second polymeric material. In another embodiment, different colors, such as for example alternating inherent color and red or blue, may be injected in intervals corresponding to 5 or 10 cm of catheter length.

The injection sprout 102 is positioned at the proximal end of the mold cavity 101. The injection sprout is positioned such that it delivers the material in the proximodistal direction into the mold cavity 101 from the proximal apex of the mold cavity 101. The mold cavity is defined by a mold 103 and a mold insert 104. The mold insert 104 comprises a mold core 105 and a displaceable mold cavity wall 106. The displaceable mold cavity wall 106 may be displaced distally into an end position, in which the mold cavity corresponds in form to the full catheter. In the start position, as illustrated in FIG. 1, the displaceable mold cavity wall 106 will be positioned and be in contact with the inner mold cavity wall and the mold core 105. At the proximal zone of the mold cavity 101 pins 107 extend transversally into contact with the mold core 105, to form drainage openings in the injection molded catheter. These pins 107 further aids in stabilizing the core during injection molding, even though they aid in a limited way when the end position is reached.

Figure 2:
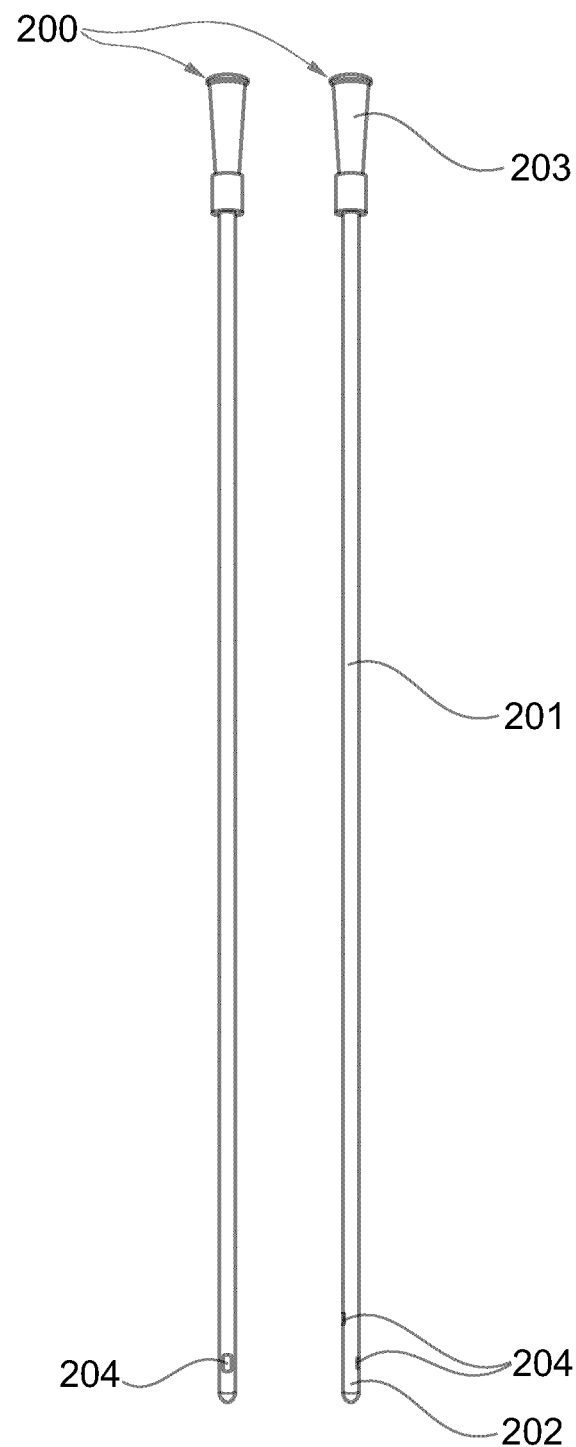
FIG. 2 is a side-view of an elongated tubular member according to one embodiment of the present invention.

The mold 103 and the mold insert 104 forms a mold cavity 101 which allows for the production of an injection molded urinary catheter 200 with a tubular body portion 201 with a rounded or slanting proximal tip portion 202 and an enlarged distal connecting portion 203, in accordance with FIG. 2. The tip portion 201 is rounded or slanting to ease insertion of the catheter 200 into the urethra. The tip portion 201 may also be olive shaped, such as to form a olive-tipped catheter. The enlarged distal connecting portion 203 is configured to allow for connection to a hose or urine evacuator. The tubular body portion 201 is thus positioned in between the proximal tip portion 202 and the enlarged distal connecting portion 203. At the proximal end zone of the catheter 200 drainage openings or drainage eyes 204 are positioned. The drainage openings 204 are preferably positioned on opposite sides of the tubular body portion, such that liquid, such as urine, may enter the catheter 200 from different directions. Due to the configuration of the mold assembly 100 a catheter with monolithically formed parts may be injection molded. This means that catheter 200 monolithically comprises the tubular body portion 201 with the rounded or slanting proximal tip portion 202, the enlarged distal connecting portion 203, said tubular body portion 201 being provided with at least one drainage opening 204 at its proximal end zone, since the catheter 200 may be injection molded in the mold assembly 100, thus eliminating the need for subsequent steps of adding a connecting portion or drainage openings. In this context "monolithic"/"monolithically" means that there is no interface, seam, weld, post-fabricated joint between the individually identified parts. Additionally, the obtained catheter 200 may have an angle between a central axis of the tubular body portion 201 and the wall of the tubular body portion 201, in a cross section along said central axis, that is below 0.5 degrees, such as cylindrical. The variation with regard to the wall thickness over the tubular body portion 201 may be kept as low as below 1/50 mm, due to the decreased vibrations of the mold core during injection.

The mold cavity 101 of the mold 103 is elongated in the proximodistal direction, with a circular transversal cross-section, and a negatively rounded or concave proximal end (bottom), while the mold core 105 also is elongated in proximodistal direction and cylindrical, i.e. a circular transversal cross-section. The difference in diameter between the diameter of the mold cavity 101 transversal cross-section and the mold core cylinder corresponds to the thickness of the catheter wall, and the diameter of the mold cavity 101 transversal cross-section corresponds to the outer circumferential catheter diameter. Usually catheters used as urinary draining devices are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus 8 FR corresponds to a catheter with an outer diameter of 2.7 mm and 18 FR corresponds to a catheter with an outer diameter of 6 mm. Thus, the outer circumferential diameter of a catheter is normally selected in the range from 2.5 mm to 10 mm, such as 3 to 6. The length of the tubular body portion of a catheter is normally selected in the range from 5 to 50 cm, such as for example 30 to 50 cm for male catheters and 5 to 15 cm for female catheters. In one embodiment the length of the catheter is approximately 40 cm, such as 40 cm, for a male catheter and approximately 11 cm, such as 11 cm, for a female catheter.

The transversal cross-sections of the mold cavity 101 and the mold core 105 may of course have other shapes than circular, such as oval, triangular, square, or multi-angular, if a specific usage calls for such other transversal cross-sections.

The mold core 105 extends proximally to the proximal apex of the mold cavity 101 to a distance from the proximal apex corresponding to the catheter thickness of the tip portion 202 of the urinary catheter to be produced. The displaceable mold cavity wall 106 is arranged between the mold 103 and the mold core 105 as a part of the mold insert 104, such that it may be displaceable distally and proximally along the surfaces thereof. The displaceable mold cavity wall 106 is slanting distally in the lateral direction. In the starting position the displaceable mold cavity wall 106 is positioned in close proximity of a proximal tip of the mold core 105, as illustrated in FIG. 1.

The displaceable mold cavity wall 106 is the proximal end wall of a mold core runner 108. The mold core runner 108 is displaceable along the cylindrical wall of the mold core 105 and the tubular wall of the mold cavity 101, said tubular part corresponding to the tubular body portion 201 of the catheter 200. The mold core runner 108 runs at the cylindrical wall of the mold core 105 via a running flange 109. Distally of the running flange 109, laterally of the mold core 105 and centrally of the mold core runner 108, a column or cavity 110 extends distally. This column/cavity 110 allows for low friction between the mold core 105, mold core runner 108 and mold 103. Also, the column/cavity 110 is in fluid communication with a pressure chamber (not shown). Once the urinary catheter has been injection molded and the mold insert 104 and molded catheter thereon are removed from the mold cavity 103, the pressure chamber may expel gas through the column/cavity 110 into the catheter, to facilitate removal of the catheter from the mold insert 104. This will be explained in more detail below, with respect of the finalization of the manufacturing process of the urinary catheter.

During manufacturing of the catheter, the plastic material, such as polyurethane, is injected into the mold cavity 101, with a mold 103 and a mold insert 104, said mold insert comprising a mold core 105 and mold core runner 108, and said mold 103, mold insert 104 with said mold core 105 and said mold core runner 108 being in said start position in accordance with FIG. 1. In FIG. 1 the injection molding start position with a start volume of the mold cavity 101 is thus illustrated. The plastic material then fills the proximal start volume of the mold cavity 101 in said start position. The filling of the start volume of the mold cavity 101 can be envisioned by the magnified left portion of FIG. 1, wherein the mold core runner 108 can be seen in close relationship with top portion pins 107, this start volume being the tip portion of the catheter being filled initially. In this position the mold core 105 is stabilized by the mold core runner 108, due to the interaction between the running flange 109 of the mold core runner 108 and the mold core 105 and mold 103, respectively. In this way vibration of the mold core 105 due to whirling of the plastic material may be decreased or minimized.

When the start volume is filled with plastic material and plastic material still is introduced through the injection sprout 102, the plastic material will displace the mold core runner 108 distally along the mold core 105 and the mold cavity wall of the mold 103. In this way the mold cavity 101 is continuously increased while the mold cavity 101 is filled with plastic material. Hence, the plastic material will aid in stabilizing the mold core 105 during the injection molding on the proximal side of the displaceable mold cavity wall 106 while the mold core runner 108, and in particularly the running flange 109, stabilizes the mold core 105 on the distal side of the displaceable mold cavity wall 106, and since there is no plastic material distally of the displaceable mold cavity wall 106 vibrations of the mold core 105 on this location will not affect the quality of the final product.

Figure 3:
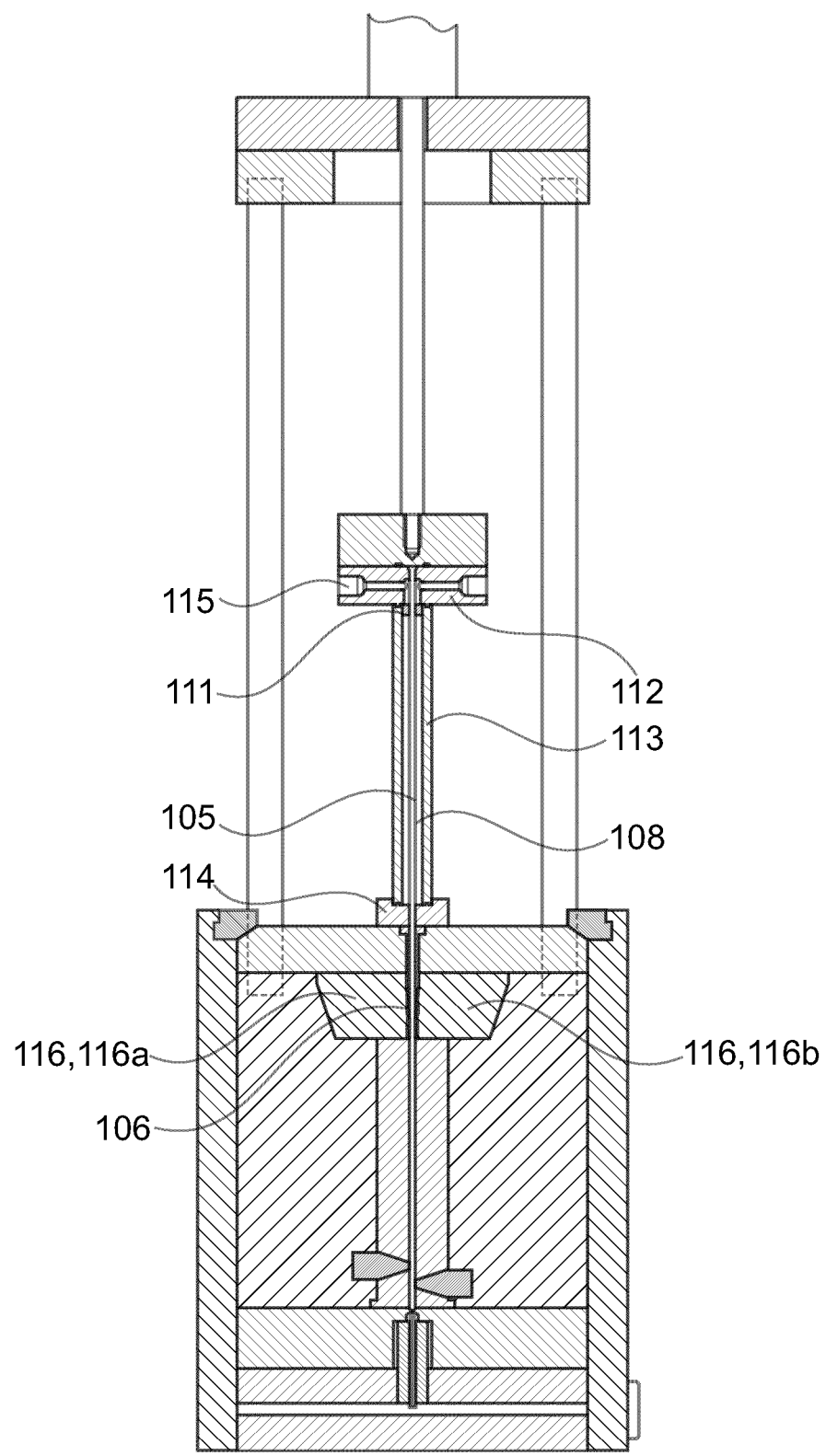
FIG. 3 is a cross-sectional view of a mold assembly according to one embodiment of the present invention.

In accordance with FIG. 3, the displaceable mold cavity wall 106 will be displaced distally until the distal end of a stop plate 111 on the mold core runner 108 hits a distal end wall 112 of a carrying cylinder 113, at the end position, in the volume of which the mold core runner 108 runs on the mold core 105. Likewise, the proximodistal extension of the cylinder 113 corresponds to the length of the catheter to be molded, such that when the stop plate 111 hits a proximal end wall 114 of the carrying cylinder 113, the mold core runner 108 will be in the start position.

The volume of the carrying cylinder 113 may be sealed of, and connected to a valve 115. The resistance of the valve 115 may be suitably selected in relation to the injection force of the injected plastic material, such that the mold core runner 108 will run smoothly and in appropriate speed for the plastic material to fill the mold cavity 101 from the start position to the end position.

Figure 4:
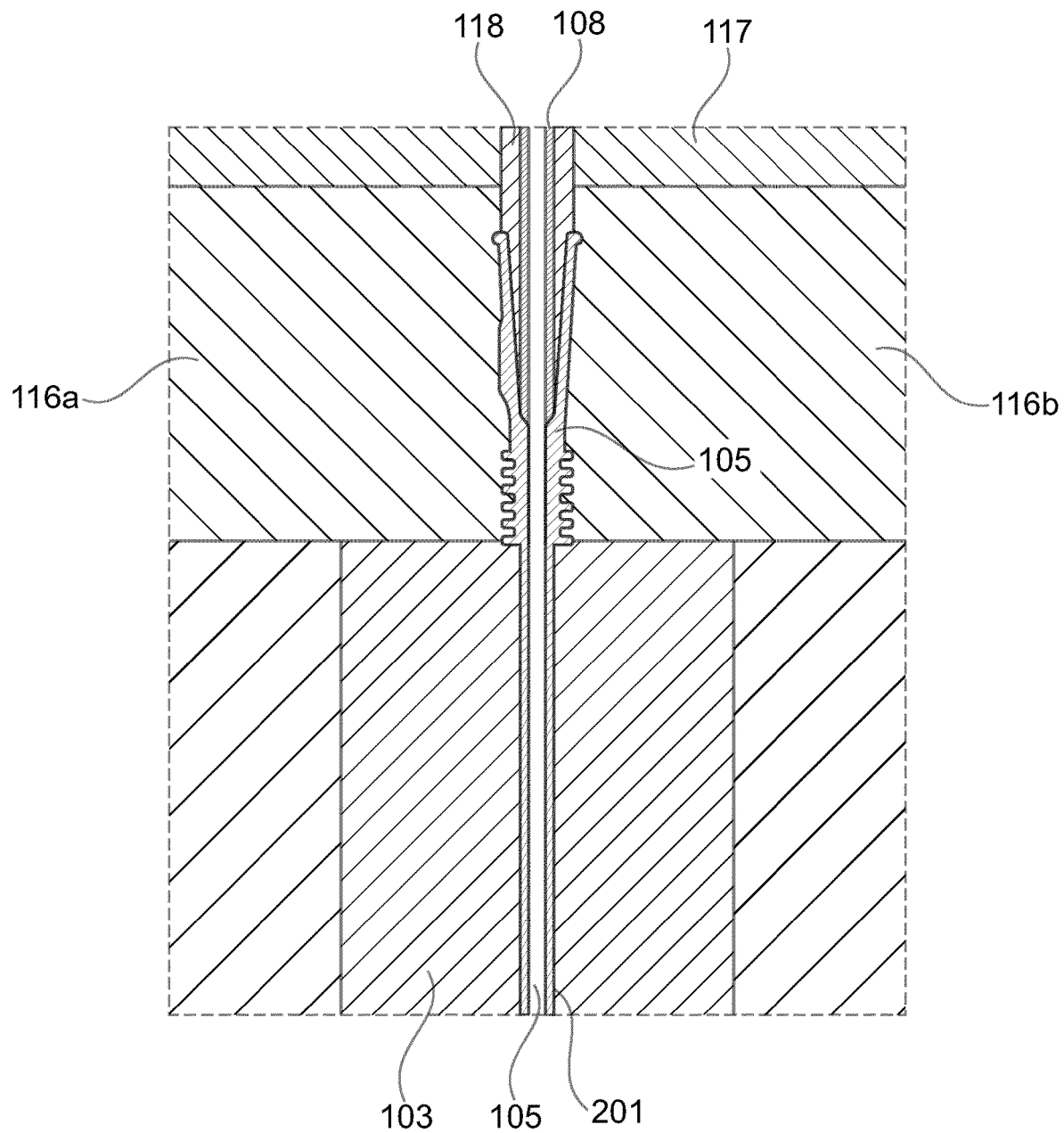
FIG. 4 is a cross-sectional view of a mold assembly according to one embodiment of the present invention.

In accordance with FIG. 4, at a distal end section of the mold cavity 101 the transversal cross-section of the mold cavity increases laterally in a distal mold part 116 corresponding to the connecting portion 203 of the catheter. The distal mold part 116 comprises two mold halves 116a, 116b. The mold halves 116a, 116b are slidingly engaged with distal mold end block 117, such that the mold halves 116a, 116b may be slid laterally after the catheter 200, mold insert 104, and the mold halves 116a, 116b has been retracted from the mold 103. The transversal cross-section first increases in the distal direction in a step wise into a tubular part of the connecting portion, and then continuously into a cone-shaped part of the connecting portion. In this way, it may be assured that the catheter is displaced distally from the mold cavity 101 together with the distal mold end block 117 and a conical mold end block protrusion 118, extending into the mold cavity 101.

Figure 5:
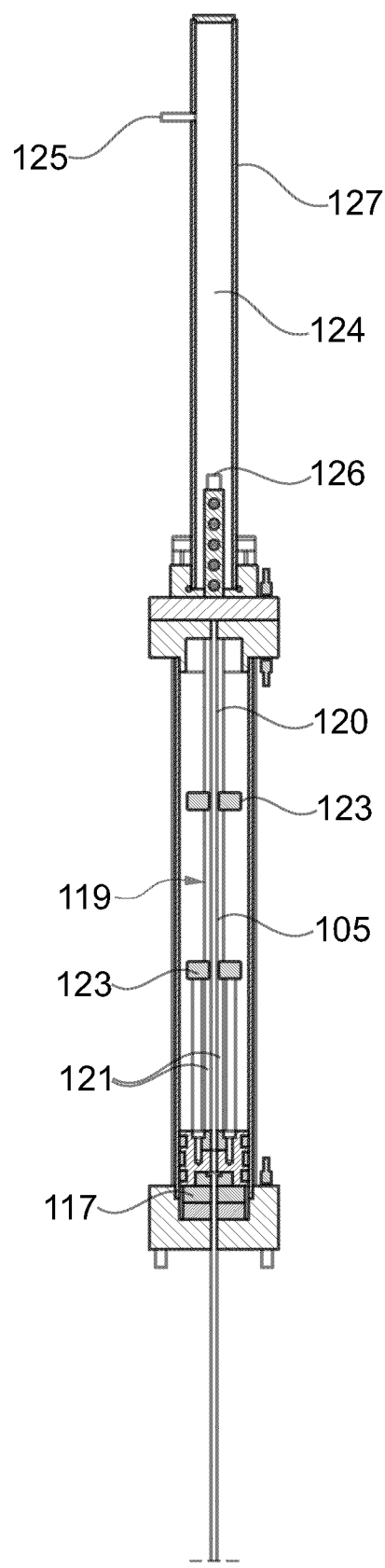
FIG. 5 is a cross-sectional view of a mold assembly according to one embodiment of the present invention, said embodiment further comprising a core guide support.

Since the mold core runner 108 is displaceable in the distal direction, the mold core 105 needs to also extend distally of the mold cavity, such as to allow for the mold core runner 108 to be slidingly displaced along the mold core 105 also outside and distally of the mold cavity 101. Thus, the core 105 also extends distally of the end block 117. Distally of the end block 117, and attached thereto, such as through screw or bolt retention, a core guide support 119 may be arranged, in accordance with FIG. 5. The guide support 119 may be arranged when the mold core 105 has a diameter of 10 mm or less, to ensure that the core mold can withstand the pressure exerted from the injected plastic material.

The core guide support 119 has a core shoot 120, adapted in size and dimensions to let the core 105 slide displaceably therein. To obtain the core shoot 120, the core guide support 119 may comprise two or more longitudinal support elements 121, arranged to form the core shoot 120 centrally thereof. For this reason the longitudinal support elements 121 may comprise a centrally arranged concave core interaction surface 122, such that the core more safely may be displaced between the longitudinal support elements 121, as disclosed in FIG. 6. The longitudinal support elements 121 are supported from lateral relational movement through shaft stays 123, in accordance with FIG. 7. The shaft stays 123 may be placed spaced apart. The shaft stays 123 may preferably be placed at regular intervals along the longitudinal support elements 121. Since the core guide support moves distally in synchronization with the distal movement of the displaceable mold cavity wall 106, there is no homogenous distal end wall of the carrying cylinder 113. Instead, an additional enclosed space 124 is arranged distally of the carrying cylinder 113, which is adapted to house the extension of the longitudinal support elements 121 when the displaceable mold cavity wall 106 is at the end position.

As for the embodiment, disclosed in for example FIG. 3, wherein the volume of the carrying cylinder 113 could be sealed off, also the carrying cylinder 113 and the space 124 can be sealed of and connected to a valve. The resistance of said valve may be suitably selected in relation to the injection force of the injected plastic material, such that the mold core runner 108 and the longitudinal support elements 121 will run smoothly and in appropriate speed for the plastic material to fill the mold cavity 101 from the start position to the end position. In the distal mold part corresponding to the connecting portion 203, the mold core runner 108 will no longer bear on the mold 103 but only on the mold core 105. Additionally, the proximal end of the mold core runner 108 will reach the end position before reaching the distal end of the mold cavity 101. This means that the displaceable mold cavity wall 106 will be positioned proximally of the distal mold cavity surface of the mold end block 117 and the conical mold end block protrusion 118. The injected material will then be distributed between the mold core runner 108 and the mold 103, in form of the mold halves 116a, 116b at the distal end zone of the mold cavity 101 and the block protrusion 118 and the mold halves 116a, 116b. In this way a the distal portion of the molded element, i.e. the catheter, will be provided with the distal connecting portion with enlarged inner and outer diameter in relation to the tubular body portion in between the proximal tip portion and the distal connecting portion. Also, a connecting portion may be obtained on the catheter without the use of a separate manufacturing step of fusing the catheter with a connecting portion, once the catheter has been injection molded. Since the injected material in this way will be distributed laterally of the mold core runner 108, the mold core runner may be benefit from an additional mechanical distal withdrawal, in addition to the pushing force from the injected material. This may be accomplished by providing a sensor 125, such as a magnetic sensor, along and distally of the mold core runner 108, and a sensible object 126, such as a magnet, on the mold core runner 108 or the core guide support 119. For example, the sensor 125 may be arranged on the casing 127, enclosing the additional enclosed space 124, at the distal end zone of the mold assembly 100, while the sensible object 126 is arranged at the end of the core guide support 119. The distance between the sensor 125 and the sensing object 126 is such that the sensible object 126 will be sensed by the sensor 125 when the displaceable mold cavity wall 106 enters the distal mold part corresponding to the connecting portion 203. When the sensor 125 senses the sensible object 126, an additional mechanical distally directed force is applied, which helps the mold core runner 108 to overcome the additional frictional force between the injected material and the mold core runner, such that the displaceable mold cavity wall 106 may be fully withdrawn until hitting the mold end block protrusion 118.

Figure 8:
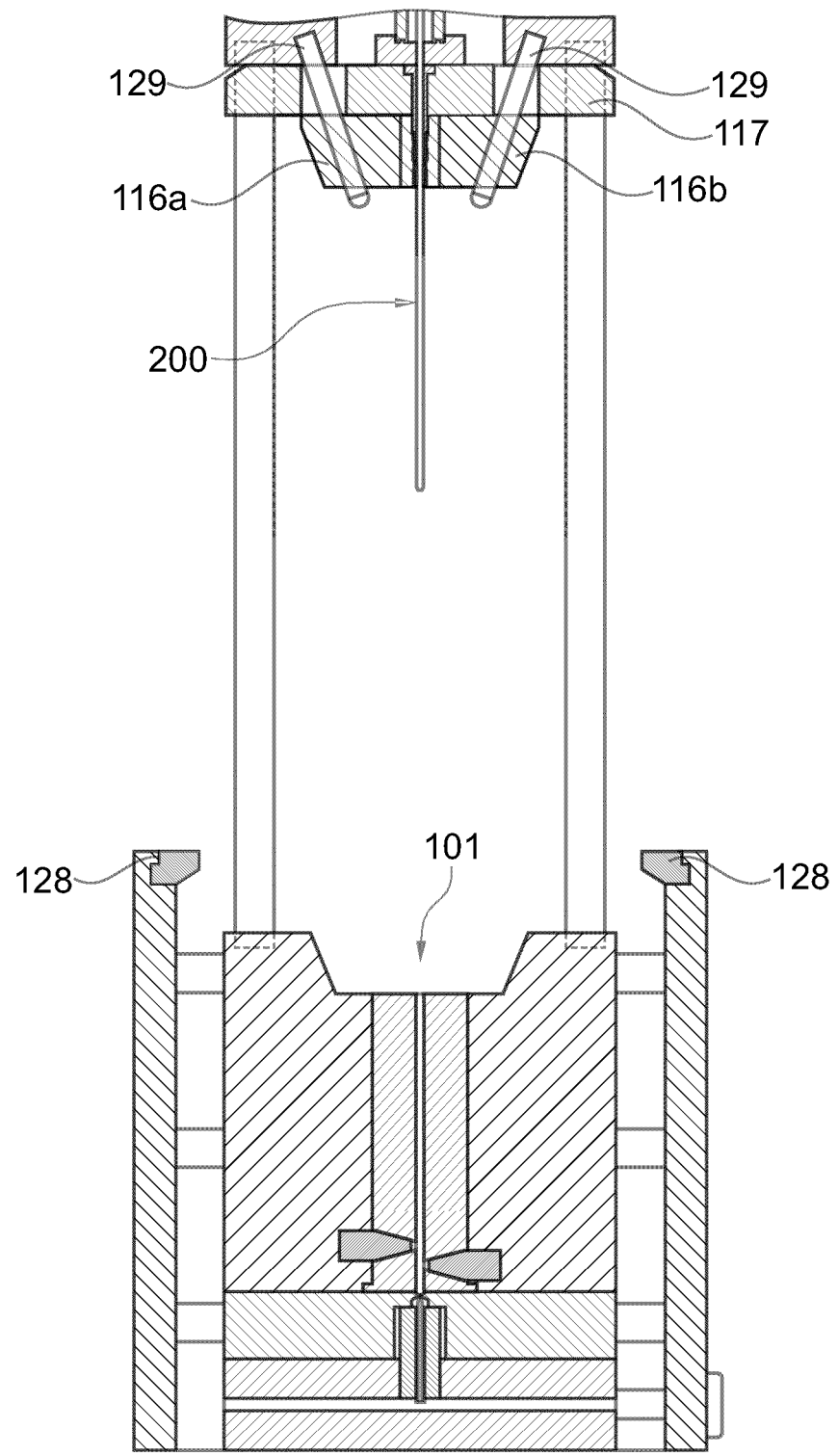
FIG. 8 is a cross-sectional view of a mold assembly according to one embodiment of the present invention.

In FIG. 8 it is disclosed when the catheter 200 has been retracted from the mold cavity 101 by the aid of suitable hydraulics or a step motor. This step is initiated by releasing the mold end block 117, and thereby also the distal mold part 116 and the conical mold end block protrusion 118. The release of these components is realized by moving lock leaves 128 laterally and perhaps distally, said lock leaves 128 during injection between the start and end position locking the mold end block 117, and thereby also the distal mold part 116 and the conical mold end block protrusion 118 from distal movement as a result of the injection force. When the mold end block 117, the distal mold part 116 and the conical mold end block protrusion 118 are moved distally, a slanting passage in the mold end block 117 will be penetrated by guiding pins 129. The guiding pins 129 are also slanting centrally in the proximal direction, so as to force the mold parts 116*a*, 116*b* laterally and thereby free the catheter 200.

In this position a flow of fluid, such as a gas or a liquid, may be forced through the column/cavity 110 in the proximal direction. Since the mold core runner 108 in this position is located within the connecting portion 203, and simultaneously being sealed of from the environment and not being clamped between the mold core 105 and the mold 103, the fluid flow will force the fluid past the running flanges 109 and proximally along the mold core 105, such that the catheter is loosened from the mold core 105.

In one embodiment the mold insert does not have a mold core runner, such that the mold cavity is of a static volume. In such an embodiment, the mold core may be provided with an inner column/cavity, which in regard to all other aspects of the embodiments disclosed above is positioned in the same way and able to provide the same technical effects, with the mere difference that there is no displaceable distal end cavity wall.

In another embodiment the mold insert does not have a column/cavity for expelling a fluid into the catheter once the catheter has been separated from the mold cavity, such that the mold cavity still may be increased continuously from a start to an end position, in accordance with all other aspects of the embodiments disclosed above is positioned in the same way and able to provide the same technical effects.

As an alternative, or in combination of, the displaceable mold cavity wall 106, the mold core 105 can be stabilized through a plurality of thin stabilizing pins (not shown) along the length of the mold core 105 inside the mold cavity 101. After initiating injection of the plastic material into the mold cavity, the thin stabilizing pins are withdrawn laterally from the mold cavity 101, such that the injected material is allowed to also fill the small eyelets formed by the thin stabilizing pins before the injected material is cured.

Although the present invention has been described above with reference to specific embodiments, it is not intended to be limited to the specific form set forth herein. Rather, the invention is limited only by the accompanying claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method for manufacturing an elongated element having a tubular body and a lumen, comprising steps of:
arranging a molding cavity, defined by a mold and a mold insert, said mold insert comprising a mold core and a displaceable mold cavity wall, said displaceable mold cavity wall being arranged between the mold and the mold core, such that the molding cavity has a start volume in a start position of the displaceable mold cavity wall;
injecting a liquid material into a proximal end of the molding cavity;
displacing the displaceable mold cavity wall, distally during said step of injecting, while keeping the mold and the mold core stationary, to increase the molding cavity volume from the start volume into an end volume at an end position of the displaceable mold cavity wall, wherein the molding cavity in said end position of the displaceable mold cavity wall corresponds to the elongated element, and wherein the step of displacing the displaceable mold cavity wall includes sliding the displaceable mold cavity wall along the mold core;
stabilizing the mold core in the start position and during distal displacement of the displaceable mold cavity wall with pins at the proximal end of the mold cavity, said pins extending transversally into contact with the mold core;
solidifying said liquid material to form the elongated element having a tubular body and a lumen;
removing the elongated element and the mold insert from the mold; and
removing the elongated element from the mold insert, and wherein said pins form drainage openings in the elongated element.

2. The method according to claim 1, wherein the displaceable mold cavity wall is the proximal end wall of a mold core runner, which is displaceable along and in relation to the mold and the mold core, said mold core runner extending longitudinally along and circumferentially of the mold core.

3. The method according to claim 1, wherein the displaceable mold cavity wall is slanting distally in a lateral direction.

4. The method according to claim 1, further comprising positioning, in the starting position, the displaceable mold cavity wall essentially adjacent a proximal tip of the mold core.

5. The method according to claim 2, further comprising positioning, in the starting position, the displaceable mold cavity wall essentially adjacent a proximal tip of the mold core and distally of the pins.

6. The method according to claim 1, further comprising injecting a fluid in the interface between the elongated element and the mold core as a part of the removal of the elongated element from said mold insert after the elongated element has been removed from said mold.

7. The method according to claim 6, wherein the fluid is injected via a column or cavity extending longitudinally in the mold insert.

8. The method according to claim 1, further comprising stabilizing the mold core distally of the displaceable mold cavity wall via a core guide support.

9. The method according to claim 8, wherein the core guide support comprises a core shoot, adapted in size and dimensions to let the mold core slide displaceably therein.

10. The method according to claim 9, wherein two or more longitudinal support elements are arranged to form the core shoot centrally thereof.

11. The method according to claim 10, wherein the longitudinal support elements comprise a centrally arranged concave core interaction surface, such that the mold core is constructed to run along said interaction surface.

12. The method according to claim 10, wherein the longitudinal support elements are supported from lateral relational movement through shaft stays.

13. The method according to claim 1, further comprising applying an additional distal withdrawal force when the displaceable mold cavity wall enters a distal end of the molding cavity.

14. The method according to claim 13, wherein said step of applying an additional distal withdrawal force comprises sensing the position of the displaceable mold cavity wall in relation to the molding cavity via a sensor and a sensible object outside the molding cavity.

15. The method according to claim 14, wherein the sensor is a magnetic sensor and the sensible object is a magnetic object.

* * * * *

UNITED STATES PATENT AND TRADEMARK OFFICE
CERTIFICATE OF CORRECTION

PATENT NO. : 10,807,287 B2
APPLICATION NO. : 14/381110
DATED : October 20, 2020
INVENTOR(S) : Erik Rolsted et al.

Page 1 of 1

It is certified that error appears in the above-identified patent and that said Letters Patent is hereby corrected as shown below:

On the Title Page

Item (71) "Applicants", delete "Eric Rolsted, Farum (DK); Jakob Øelund, Allerød (DK); Lars Olav Schertiger, Fredensborg (DK); Preben Luther, Birkerød (DK); Kim Bager, Lyngby (DK)".

In the Specification

In Column 2, Line 41, delete "of" and insert -- of: --, therefor.

In Column 3, Line 4, delete "is across-sectional" and insert -- is a cross-sectional --, therefor.

In Column 4, Line 65, delete "201" and insert -- 202 --, therefor.

In Column 4, Line 67, delete "201" and insert -- 202 --, therefor.

In Column 7, Line 8, delete "sealed of," and insert -- sealed off, --, therefor.

In Column 8, Line 2, delete "sealed of" and insert -- sealed off --, therefor.

In Column 8, Line 22, delete "a the" and insert -- a --, therefor.

In Column 9, Line 8, delete "sealed of" and insert -- sealed off --, therefor.

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*